United States Patent
Zheng et al.

(10) Patent No.: US 11,890,397 B1
(45) Date of Patent: Feb. 6, 2024

(54) HIGH ANTICOAGULATION EXTRACORPOREAL CIRCULATION TUBE

(71) Applicant: Wenzhou Safety (Emergency) Research Institute, Tianjin University, Wenzhou (CN)

(72) Inventors: Bin Zheng, Wenzhou (CN); Haojun Fan, Wenzhou (CN); Bowen Li, Wenzhou (CN); Tingting Hua, Wenzhou (CN)

(73) Assignee: Wenzhou Safety (Emergency) Research Institute, Tianjin University, Wenzhou (CN)

( * ) Notice: Subject to any disclaimer, the term of this patent is extended or adjusted under 35 U.S.C. 154(b) by 0 days.

(21) Appl. No.: 17/948,711

(22) Filed: Sep. 20, 2022

(30) Foreign Application Priority Data

Aug. 24, 2022 (CN) .......................... 202211017068.1

(51) Int. Cl.
| | | |
|---|---|---|
| *A61L 33/00* | (2006.01) | |
| *A61L 27/34* | (2006.01) | |
| *C08L 27/06* | (2006.01) | |
| *C08L 69/00* | (2006.01) | |

(52) U.S. Cl.
CPC .......... *A61L 33/0029* (2013.01); *A61L 27/34* (2013.01); *A61L 33/0041* (2013.01); *C08L 27/06* (2013.01); *C08L 69/00* (2013.01); *A61L 2420/02* (2013.01)

(58) Field of Classification Search
CPC .................................................. A61L 33/0029
See application file for complete search history.

(56) References Cited

FOREIGN PATENT DOCUMENTS

| CN | 105311974 A | 2/2016 |
|---|---|---|
| CN | 207384541 U | 5/2018 |
| CN | 209451036 U | 10/2019 |

*Primary Examiner* — Dah-Wei D. Yuan
*Assistant Examiner* — Andrew J Bowman
(74) *Attorney, Agent, or Firm* — Nitin Kaushik

(57) ABSTRACT

Disclosed is a high anticoagulation extracorporeal circulation tube, which include the following preparation methods: S1, firstly, aminating the surface of the tube by extrusion molding; S2, activating heparin groups by a direct coupling method; S3, heparinizing PVC or PC tubes; S4, then, using albumin, functionalized PEG which can react with amino groups, and phosphate to further surface modify the inner wall of heparinized PVC or PC tube to block the sites not modified by heparinization, so as to shield the adsorption of platelets and protein in blood on the inner wall. The application can produce a novel high anticoagulation extracorporeal circulation tube with low price and high biocompatibility, which expands the application in clinic.

9 Claims, 5 Drawing Sheets

HIGH ANTICOAGULATION EXTRACORPOREAL CIRCULATION TUBE

CROSS-REFERENCE TO RELATED APPLICATIONS

The application claims priority to Chinese patent application No. 202211017068.1, filed on Aug. 24, 2022, the entire contents of which are incorporated herein by reference.

TECHNICAL FIELD

The application relates to the technical field of hemodialysis circulation tube, in particular to a high anticoagulation extracorporeal circulation tube.

BACKGROUND

At present, the development of cardiac surgery drives the research and application of biomedical materials. Cardiopulmonary bypass, dialysis and hemofiltration urgently need the development and application of related biomedical materials. The application of biomaterials faces two major problems: biocompatibility and blood compatibility. Biological materials in contact with blood will stimulate the host defense mechanism, especially the blood stabilization mechanism, which will cascade and cause thrombosis and embolism, which will seriously endanger the patient's life. It is necessary to develop a high anticoagulation extracorporeal circulation tube.

However, at present, there are some consumables for extracorporeal circulation with heparinized coating, which have poor anticoagulation effect due to the easy shedding of anticoagulations. Therefore, a kind of high anticoagulation extracorporeal circulation tube is urgently needed.

SUMMARY

The present application provides a high anticoagulation extracorporeal circulation tube to solve the problems mentioned in the background technology.

To achieve the above objective, the present application adopts the following technical scheme:

A high anticoagulation extracorporeal circulation tube, including the following preparation methods:

S1, firstly, aminating the surface of the tube by extrusion molding, mixing PC or PVC plastic raw materials with raw materials rich in amino functional groups, adding the mixture into a hopper of an extrusion molding machine, and then entering the space of the screw groove by self-weight or under the action of a forced feeder, and moving to the machine head under the push of the screw ribs, wherein all raw materials will be conveyed forward by one lead every time the screw rotates; meanwhile, in the extrusion process, discharging the gas between the raw materials from the hopper by compressing, finally melting, cooling and molding, and cutting or cutting off as required, thus completing the grafting of raw materials rich in amino functional groups to the inner wall of the pipe, and washing to obtain PVC or PC tube rich in amino groups;

S2, activating heparin groups by a direct coupling method, dissolving heparin sodium in citric acid buffer, adding 1-(3-dimethylaminopropyl)-3-ethylcarbodiimide or EDC and NHS, and stirring the solution in an ice-water bath for 1-5 h to activate the active groups of heparin to generate activated heparin containing carboxyl groups;

S3, heparinizing the PVC or PC tube, adding carboxylated heparin solution into the PVC or PC tube containing amino groups, refluxing for 1-20 hours, discharging the solution, repeating this step for 1-3 times, after the reaction, washing the PVC or PC tube in the mixed solution of ethanol and distilled water for 1-3 times, each time for 10-100 minutes, removing physically adsorbed heparin and other impurities, and then placing the PVC or PC tube in a vacuum drying oven and drying.

S4, after the heparinization of the PVC or PC tube is completed, using albumin, functionalized PEG which can react with amino groups, and phosphate to further surface modify the inner wall of heparinized PVC or PC tube to block the sites not modified by heparinization, so as to shield the adsorption of platelets and protein in blood on the inner wall.

As a further improvement of the technical scheme, in S1, the raw materials rich in amino functional groups include any one or more of PEI, chitosan, polylysine, ethylenediamine, urea-formaldehyde, aniline and amino-terminated hyperbranched polyamide, and the ratio of the raw materials rich in amino functional groups to the PC or PVC plastic raw materials is 0.001%-10%.

As a further improvement scheme of the technical scheme, in S1, after the reaction, characterizing the amino loading effect by FT-IR and water contact angle measurement, and observing whether the amino characteristic peak appears in the FT-IR spectrum and the water contact angle decreases.

As a further improvement of the technical scheme, in S2, the mass percentage concentration of the heparin sodium is 1%-50%, the PH of the citric acid buffer is 3.0-6.0, and the mass percentage concentration of the 1-(3-dimethylaminopropyl)-3-ethylcarbodiimide or EDC and NHS is 0.001%-10%.

As a further improvement of the technical scheme, in S3, the concentration ratio of ethanol and distilled water is 1:99-99:1 in the mixed solution, so as to efficiently clean unreacted monomers or possible residual harmful components in the PVC or PC tube.

As a further improvement scheme of the technical scheme, in S4, using a plurality of anticoagulation methods to further surface modify the inner wall of heparinized PVC or PC tube, including albumin modification, functionalized PEG modification and phosphate modification, and the concentration of the modified raw materials is $1\times10^0$ ug/ml~$1\times10^6$ ug/ml.

As a further improvement scheme of the technical scheme, the albumin modification is to modify the surface of the heparinized PVC or PC tube with an enhancer containing albumin, so as to effectively reduce thrombosis on the surface of the heparinized PVC or PC tube.

As a further improvement scheme of the technical scheme, the functionalized PEG includes any one or more of active carboxylated PEG, PEG containing succinimide ester, PEG containing isothiocyanine group and PEG containing sulfonyl chloride group, using the functionalized PEG to modify the surface of heparinized high anticoagulation PVC or PC tube to reduce the interaction between the inner surface of the heparinized high anticoagulation PVC or PC tube and blood components.

As a further improvement scheme of the technical scheme, the phosphate modification is to modify the inner wall of the heparinized PVC or PC tube with a phosphate-containing reinforcing agent, so as to effectively reduce the adsorption of platelets and protein on the inner surface of the heparinized PVC or PC tube.

Compared with the prior art, the present application has the advantages that:

Firstly, organic solvent and amino raw materials are mixed and added into PVC/PC tube to graft amino groups on its surface, so that a large amount of amino groups are loaded on the tube's surface. Then EDC/NHS is used to catalyze heparin to generate heparin containing carboxyl groups, and heparin is covalently bonded to the inner surface of the PVC/PC tube through the reaction of carboxyl groups on heparin molecules and amino groups on the inner surface of the PVC/PC tube, so that heparinization is more stable. After that, anticoagulation enhancer is used to modify the tube, and finally the anticoagulation effect of the PVC/PC tube as ECMO blood circulation tube is significantly improved, and the usable time is at least half a month. The present application can produce a novel high anticoagulation extracorporeal circulation tube with low price and high biocompatibility, which expands the wide application in clinic, fills up the research gap in related fields.

The above description is only a summary of the technical scheme of the present application. In order to understand the technical means of the present application more clearly and implement it according to the contents of the description, the following detailed description will be given with the preferred embodiment of the present application and the accompanying drawings. The specific embodiments of the present application are given in detail by the following examples and their drawings.

BRIEF DESCRIPTION OF THE DRAWINGS

The drawings illustrated here are used to provide a further understanding of the present application and form a part of this application. The illustrative embodiments of the present application and their descriptions are used to explain the present application, and do not constitute undue limitations on the present application. In the attached drawings.

DETAILED DESCRIPTION OF THE EMBODIMENTS

The principles and features of the present application will be described with reference to the accompanying drawings. Examples are only used to explain the present application, but not to limit the scope of the present application. In the following paragraphs, the present application will be more specifically described by way of example with reference to the accompanying drawings. The advantages and features of the present application will be more apparent from the following description and claims. It should be noted that the drawings are all in a very simplified form and in inaccurate proportions, and are only used to facilitate and clearly explain the purpose of the embodiments of the present application.

It should be noted that when a component is said to be "fixed" to another component, it can be directly on another component or there can be an intermediate component. When a component is considered to be "connected" to another component, it can be directly connected to another component or there may be intervening components at the same time. When a component is considered to be "set on" another component, it can be directly set on another component or there may be an intervening component at the same time. The terms "vertical", "horizontal", "left", "right" and similar expressions used in this paper are for illustrative purposes only.

Unless otherwise defined, all technical and scientific terms used herein have the same meanings as commonly understood by those skilled in the technical field of the present application. The terminology used in this specification of the present application is only for the purpose of describing specific embodiments, and is not intended to limit the present application. As used herein, the term "and/or" includes any and all combinations of one or more related listed items.

Figure 1:
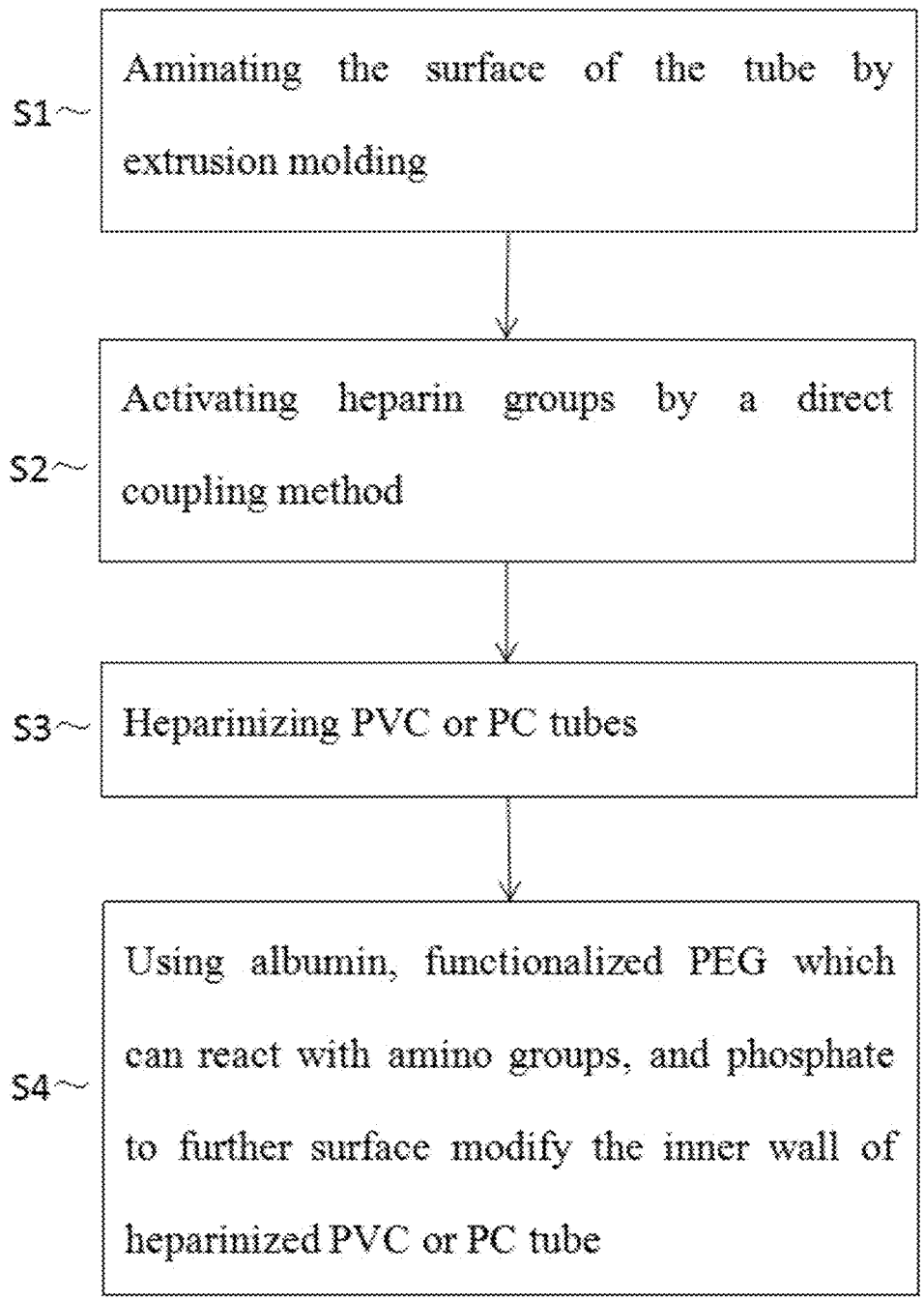
FIG. 1 is a schematic diagram of a preparation method of a high anticoagulation extracorporeal circulation tube.

Please refer to FIG. 1. In the embodiment of the application, a high anticoagulation extracorporeal circulation tube includes the following preparation methods:

S1, firstly, aminating the surface of the tube by extrusion molding, mixing PC or PVC plastic raw materials with raw materials rich in amino functional groups (PEI, chitosan, polylysine, ethylenediamine, urea-formaldehyde, aniline and amino-terminated hyperbranched polyamide, etc.). The ratio of the raw materials rich in amino functional groups to the PC or PVC plastic raw materials is 0.001%-10%. Adding the mixture into a hopper of an extrusion molding machine. The mixture enters the space of the screw groove of the screw rely on its own weight or under the action of forced feeder and moves to the machine head under the push of the screw ribs. Every time the screw rotates, all the raw materials will be transported forward for one lead. At the same time, during the extrusion process, the gas between the raw materials will be discharged from the hopper, and finally, melt-cooling and molding will be carried out, and cutting or cutting off will be carried out according to the needs, thus the raw materials rich in amino functional groups will be grafted onto the inner wall of the tube. After washing, the PVC or PC tube rich in amino groups is obtained. After the reaction, characterizing the amino loading effect by FT-IR and water contact angle measurement, and observing whether the amino characteristic peak appears in the FT-IR spectrum and the water contact angle decreases.

S2, activating heparin groups by direct coupling method, dissolving 1%~50% heparin sodium in citric acid buffer with PH of 3.0~6.0, adding 1-(3-dimethylaminopropyl)-3-ethylcarbodiimide or EDC and NHS (with mass concentration of 0.001%-10%), and stirring the solution in an ice-water bath for 1 h~5 h to activate the active groups of heparin to generate activated heparin containing carboxyl groups.

S3, heparinizing the PVC or PC tube, adding the carboxylated heparin solution into the PVC or PC tube containing amino groups, refluxing for 1-20 hours, discharging the solution, repeating this step for 1-3 times, and after the reaction, washing the PVC or PC tube in the mixed solution of ethanol and distilled water for 1-3 times (the concentration ratio of ethanol and distilled water is 1:99-99:1) each time for 10-100 minutes, removing physically adsorbed heparin and other impurities, and then placing the PVC or PC tube in a vacuum drying oven and drying.

S4, after the heparinization of the PVC or PC tube is completed, using albumin, functionalized PEG which can react with amino groups, and phosphate to further surface modify the inner wall of heparinized PVC or PC tube to block the sites not modified by heparinization, so as to shield the adsorption of platelets and protein in blood on the inner wall. Various anticoagulation methods are used to further surface modify the heparinized PVC or PC tube, including albumin modification, functionalized PEG modification and phosphate modification, and the concentration of modification raw materials is $1 \times 10^0$ ug/ml~$1 \times 10^6$ ug/ml.

Specifically, the albumin modification is to modify the surface of the heparinized PVC or PC pipe with an enhancer containing albumin, which is used to effectively reduce thrombosis on the surface of heparinized PVC or PC tube.

Specifically, the functionalized PEG includes any one or more of active carboxylated PEG, PEG containing succinimide ester, PEG containing isothiocyanine group and PEG containing sulfonyl chloride group. The functionalized PEG is used to modify the surface of the heparinized high anticoagulation PVC or PC tube, so as to reduce the interaction between the inner surface of the heparinized high anticoagulation PVC or PC tube and blood components.

Specifically, the phosphate modification is to modify the inner wall of the heparinized PVC or PC tube with a phosphate-containing reinforcing agent, so as to effectively reduce the adsorption of platelets and protein on the inner surface of the heparinized PVC or PC tube.

The working principle of the present application is:

Firstly, organic solvent and amino raw materials are mixed and added into PVC/PC tube to graft amino groups on its surface, so that a large amount of amino groups are loaded on the tube's surface. Then EDC/NHS is used to catalyze heparin to generate heparin containing carboxyl groups, and heparin is covalently bonded to the inner surface of the PVC/PC tube through the reaction of carboxyl groups on heparin molecules and amino groups on the inner surface of the PVC/PC tube, so that heparinization is more stable. After that, anticoagulation enhancer is used to modify the tube, and finally the anticoagulation effect of the PVC/PC tube as ECMO blood circulation tube is significantly improved, and the usable time is at least half a month. The present application can produce a novel high anticoagulation extracorporeal circulation tube with low price and high biocompatibility, which expands the wide application in clinic, fills up the research gap in related fields.

Figure 2:
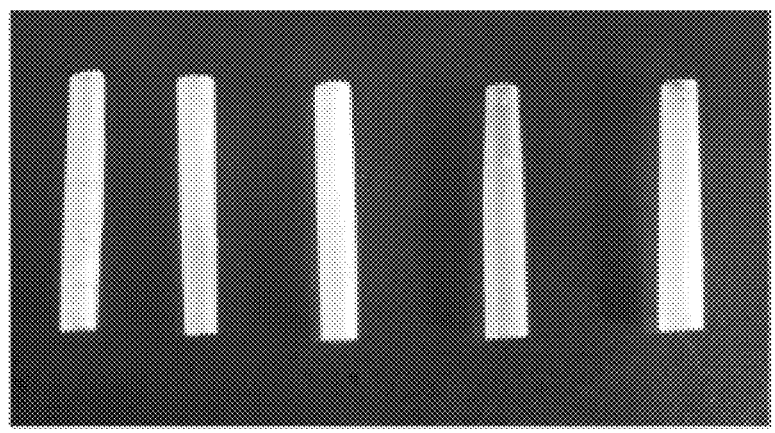
FIG. 2 is a photograph of the high anticoagulation extracorporeal circulation tubes prepared by the embodiment of the present application.

FIG. 2 is a photograph of the high anticoagulation extracorporeal circulation tubes prepared by the embodiment of the present application.

Figure 3:
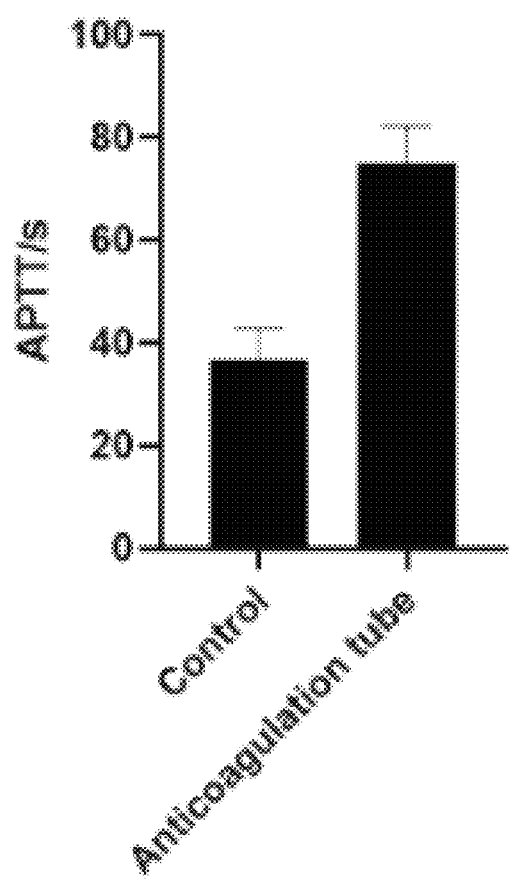
FIG. 3 is a schematic diagram of APTT (Activating partial thromboplastin time) test results of the high anticoagulation extracorporeal circulation tubes prepared by the embodiment of the present application.
Figure 4:
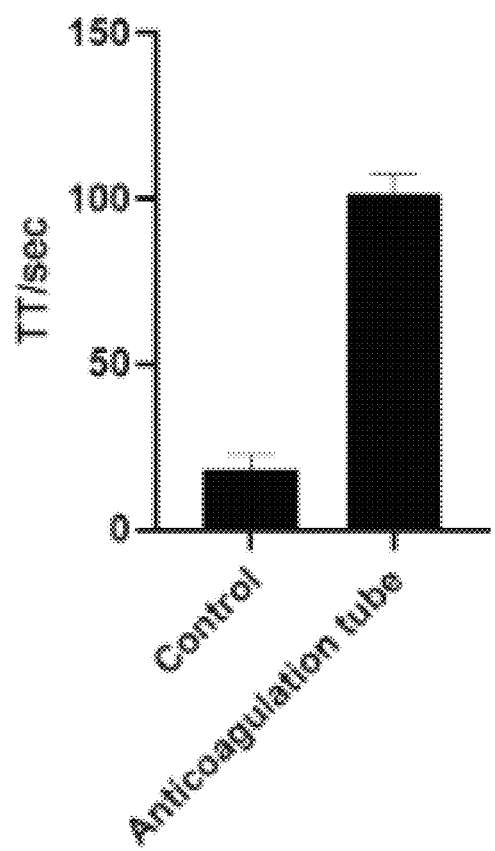
FIG. 4 is a schematic diagram of TT (Thrombin time) test results of the high anticoagulation extracorporeal circulation tubes prepared by the embodiment of the present application.
Figure 5:
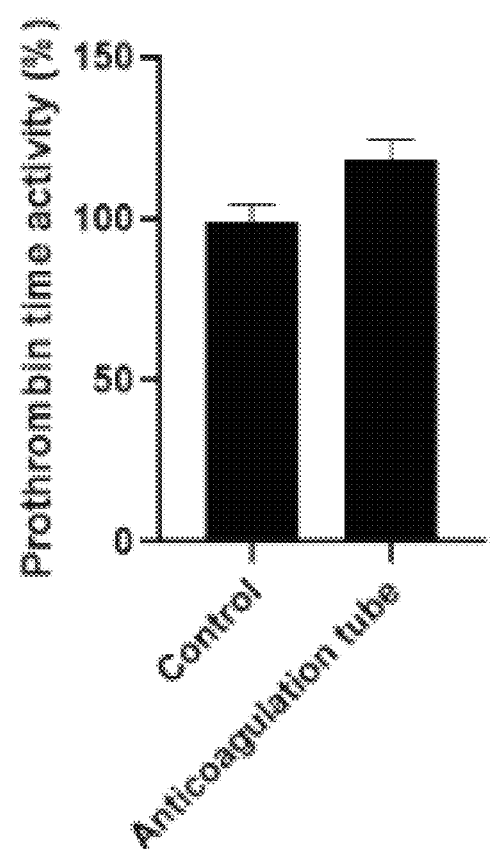
FIG. 5 is a schematic diagram of plasma prothrombin time test results of the high anticoagulation extracorporeal circulation tubes prepared by the embodiment of the present application.

FIGS. 3-5 are schematic diagrams of multiple test results of the high anticoagulation extracorporeal circulation tubes prepared by the embodiment of the present application. FIG. 3 is a schematic diagram of APTT (Activating partial thromboplastin time) test results. FIG. 4 is a schematic diagram of TT (Thrombin time) test results, and FIG. 5 is a schematic diagram of plasma prothrombin time test results.

The above description is only a preferred embodiment of the present application, and does not limit the present application in any form. Those of ordinary skill in the industry can smoothly implement the application as shown in the drawings and described above; However, those skilled in the art who make some changes, modifications and equivalent changes by using the technical contents disclosed above without departing from the scope of the technical scheme of the present application are equivalent embodiments of the present application. Meanwhile, any changes, modifications and evolutions equivalent to the above embodiments made according to the essential technology of the present application are still within the protection scope of the technical scheme of the present application.

What is claimed is:

1. A anticoagulation extracorporeal circulation tube, comprising the following preparation methods:

S1, firstly, aminating a surface of a tube by extrusion molding, mixing PC or PVC plastic raw materials with raw materials rich in amino functional groups to form a mixture, adding the mixture into a hopper of an extrusion molding machine, and then entering a space of a screw groove by self-weight or under an action of a forced feeder, and moving to a head of the machine under a push of a screw flight, wherein all raw materials are conveyed forward by one lead every time a screw rotates; meanwhile, in an extrusion process, discharging a gas between the raw materials from the hopper by compressing, finally melting, cooling and molding, and cutting or cutting off as required, completing a grafting of raw materials rich in amino functional groups to an inner wall of the tube, and washing to obtain PVC or PC tube rich in amino groups;

S2, activating heparin groups by a direct coupling method, dissolving heparin sodium in citric acid buffer, adding 1-(3-dimethylaminopropyl)-3-ethylcarbodiimide or 1-ethyl-3-(3-dimethyl aminopropyl) carbodiimide and N-hydroxysuccinimide, and stirring a solution in an ice-water bath for 1-5 h to activate a plurality of active groups of heparin to generate activated heparin containing carboxyl groups;

S3, heparinizing the PVC or PC tube, adding carboxylated heparin solution into the PVC or PC tube containing amino groups, refluxing for 1-20 hours, discharging the solution, repeating for 1-3 times, washing the PVC or PC tube in a mixed solution of ethanol and distilled water for 1-3 times, each time for 10-100 minutes, removing physically adsorbed heparin and other impurities, and then placing the PVC or PC tube in a vacuum drying oven and drying;

S4, after the heparinization of the PVC or PC tube is completed, using albumin, functionalized polyethylene glycol which can react with amino groups, and phosphate to further surface modify the inner wall of heparinized PVC or PC tube to block a plurality of sites not modified by heparinization, to shield the adsorption of platelets and protein in blood on the inner wall.

2. The anticoagulation extracorporeal circulation tube according to claim 1, wherein in S1, the raw materials rich in amino functional groups comprise any one or more of polyethyleneimine, chitosan, polylysine, ethylenediamine, urea-formaldehyde, aniline and amino-terminated hyperbranched polyamide, and the ratio of the raw materials rich in amino functional groups to the PC or PVC plastic raw materials is 0.001%-10%.

3. The anticoagulation extracorporeal circulation tube according to claim 1, wherein in S1, after a reaction, characterizing the amino loading effect by FT-IR and water contact angle measurement, and observing whether an amino characteristic peak appears in the FT-IR spectrum and the water contact angle decreases.

4. The anticoagulation extracorporeal circulation tube according to claim 1, wherein in S2, the mass percentage concentration of the heparin sodium is 1%-50%, the PH of the citric acid buffer is 3.0-6.0, and the mass percentage concentration of the 1-(3-dimethylaminopropyl)-3-ethylcarbodiimide or 1-ethyl-3-(3-dimethyl aminopropyl) carbodiimide and N-hydroxysuccinimide is 0.001%-10%.

5. The anticoagulation extracorporeal circulation tube according to claim 1, wherein in S3, the concentration ratio of ethanol and distilled water is 1:99-99:1 in the mixed solution, so as to efficiently clean unreacted monomers or possible residual harmful components in the PVC or PC tube.

6. The anticoagulation extracorporeal circulation tube according to claim 1, wherein in S4, using a plurality of anticoagulation methods to further surface modify the inner wall of heparinized PVC or PC tube, including albumin modification, functionalized polyethylene glycol modification and phosphate modification, and the concentration of the modified raw materials is $1\times10^0 \sim 1\times10^6$ ug/milliliter (ml.).

7. The anticoagulation extracorporeal circulation tube according to claim 6, wherein an albumin modification is to modify the surface of heparinized PVC or PC tube with an enhancer containing albumin, so as to reduce thrombosis on the surface of the heparinized PVC or PC tube.

8. The anticoagulation extracorporeal circulation tube according to claim 6, wherein the functionalized polyethylene glycol comprises any one or more of active carboxylated polyethylene glycol, polyethylene glycol containing succinimide ester, polyethylene glycol containing isothiocyanine group and polyethylene glycol containing sulfonyl chloride group, using the functionalized polyethylene glycol to modify the surface of heparinized anticoagulation PVC or PC tube to reduce a interaction between the inner surface of the heparinized anticoagulation PVC or PC tube and blood components.

9. The anticoagulation extracorporeal circulation tube according to claim 6, wherein a phosphate modification is to modify the inner wall of the heparinized PVC or PC tube with a phosphate-containing reinforcing agent, so as to reduce the adsorption of platelets and protein on the inner surface of the heparinized PVC or PC tube.

* * * * *